(12) United States Patent
Ziolo

(10) Patent No.: US 9,522,024 B2
(45) Date of Patent: Dec. 20, 2016

(54) ORTHOPEDIC PLATE AND SCREW APPARATUS

(71) Applicant: BLACKSTONE MEDICAL, INC., Lewisville, TX (US)

(72) Inventor: Tara Ziolo, Hewitt, NJ (US)

(73) Assignee: BLACKSTONE MEDICAL, INC., Lewisville, TX (US)

( * ) Notice: Subject to any disclaimer, the term of this patent is extended or adjusted under 35 U.S.C. 154(b) by 132 days.

(21) Appl. No.: 13/797,227

(22) Filed: Mar. 12, 2013

(65) Prior Publication Data

US 2014/0277179 A1    Sep. 18, 2014

(51) Int. Cl.
*A61B 17/80* (2006.01)
*A61B 17/86* (2006.01)

(52) U.S. Cl.
CPC ....... *A61B 17/8047* (2013.01); *A61B 17/8605* (2013.01)

(58) Field of Classification Search
CPC ................................................. A61B 17/8047
USPC ................................. 606/289, 290, 292, 293
See application file for complete search history.

(56) References Cited

U.S. PATENT DOCUMENTS

| | | | |
|---|---|---|---|
| 5,531,746 A | 7/1996 | Errico et al. | |
| 5,954,722 A | 9/1999 | Bono | |
| 6,206,881 B1 | 3/2001 | Frigg et al. | |
| 6,955,677 B2 | 10/2005 | Dahners | |
| 8,328,855 B2* | 12/2012 | Worcel | 606/290 |
| 2003/0187440 A1* | 10/2003 | Richelsoph | A61B 17/8042 606/287 |
| 2004/0127896 A1 | 7/2004 | Lombardo et al. | |
| 2005/0228386 A1* | 10/2005 | Ziolo et al. | 606/69 |
| 2006/0122604 A1 | 6/2006 | Gorhan et al. | |
| 2006/0149251 A1 | 7/2006 | Ziolo et al. | |
| 2008/0177330 A1 | 7/2008 | Ralph et al. | |
| 2009/0192553 A1 | 7/2009 | Maguire et al. | |
| 2011/0152945 A1* | 6/2011 | Matityahu | 606/290 |

OTHER PUBLICATIONS

International Search Report and Written Opinion, PCT/US2014/024703, dated Jul. 14, 2014, 10 pages.

* cited by examiner

*Primary Examiner* — Andrew Yang
(74) *Attorney, Agent, or Firm* — Baker & McKenzie LLP

(57) ABSTRACT

Example embodiments relate generally to orthopedic plate assemblies comprising a fastener, a first and second bushing, and a plate. The fastener comprises a head and an elongated body. The first bushing comprises an interior surface operable to receive the fastener head and a notch actuatable to contact against the fastener head. The second bushing comprises an interior surface operable to receive at least a portion of an exterior surface of the first bushing, an exterior surface comprising flat surface portions disposed about opposite sides of the second bushing, an upper surface, and a lower surface. The plate comprises an opening operable to receive at least a portion of the exterior surface of the second bushing, said opening comprising a pair of flat surface portions operable to contact with the pair of flat surface portions of the second bushing.

24 Claims, 5 Drawing Sheets

ORTHOPEDIC PLATE AND SCREW APPARATUS

TECHNICAL FIELD

The present disclosure relates generally to an orthopedic plate and screw apparatus.

BACKGROUND

Surgically implanted support systems and methods have long been employed to immobilize one or more bones, including those that are fractured, broken and/or structurally deteriorated.

Immobilization has been achieved through a variety of known orthopedic devices, such as those pertaining to orthopedic plate and screw assemblies. In general, a surgically implanted orthopedic plate is fixedly attached to one or more bones by threading one or more screws perpendicularly relative to the plane of the plate into corresponding openings of the plate and into the bone. Once the screws have been threaded into the bone(s), the screws serve to collectively anchor the plate to the bone(s). Conventional orthopedic plate and screw assemblies utilize orthopedic plates having two or more openings, and a corresponding number of screws. For example, orthopedic plate and screw assemblies having two, four, six, eight, or ten openings, and the same corresponding number of screws, are in widespread use to treat patients.

Conventional orthopedic plate and screw assemblies can be problematic, in certain patients and in certain situations. For example, oftentimes the proximate area of a bone receiving a screw may not be substantially flat. In such situations, if a surgeon chooses to proceed with anchoring the screw thereto, the screw will enter the bone at an angle that is not substantially perpendicular to the proximate plane of the bone. Generally, the effectiveness and/or anchoring strength of a surgically implanted orthopedic plate and screw assembly may deteriorate over time when the entry angle of one or more of its anchored screws deviates from a substantially perpendicular angle relative to the proximate plane of the bone. Undesirable consequences of such an anchored screw may include adverse near and long term affects to one or more bones, including the eventual loosening and/or backing out of the screw from the bone over time, other adverse affects to existing fractures and/or other pre-existing problematic conditions of one or more bones, and possibly even the causation of new bone fractures and/or other new problematic conditions to one or more bones.

As another example of conventional orthopedic plate and screw assembly problems, one or more anchored screws of a conventional surgically implanted orthopedic plate and screw assembly may unscrew (backout) from the orthopedic plate over time. Causes for screw backouts may include everyday movements of a recipient patient, screws undesirably anchored at entry angles that are not substantially perpendicular to the proximate plane of the bone, or the like, or combinations thereof. Generally, screw backouts may become problematic since the effectiveness and/or anchoring strength of a surgically implanted orthopedic plate and screw assembly may correspondingly deteriorate over time, causing a variety of possible undesirable consequences. For example, adverse affects may result to existing fractures and/or other pre-existing conditions of one or more bones, and possibly even the causation of new bone fractures. Furthermore, the screws may eventually come away from the bone and/or orthopedic plate altogether, causing further near and/or long term adverse affects to one or more bones, other new problematic conditions to one or more bones, and/or bruising and/or lacerations to areas surrounding the bone.

SUMMARY

It is recognized herein that the above problems can be solved by exemplary embodiments of an orthopedic plate and fastener assembly.

Present example embodiments relate generally to an orthopedic plate assembly comprising a fastener, a bushing and a plate. The fastener may comprise a head and an elongated body connected at one end to the head. The bushing comprises an interior surface operable to receive at least a portion of the fastener head and a notch operable to contact against the fastener head. The plate comprises an opening operable to receive the elongated body of the fastener and at least a portion of an exterior surface of the bushing.

In accordance with another exemplary embodiment, an orthopedic plate assembly comprises a fastener, a bushing and a plate. The bushing may comprise an interior surface operable to receive at least a portion of the fastener, an exterior surface comprising a pair of flat surface portions disposed about opposite sides of the bushing, an upper surface in communication with the interior surface and the exterior surface, and a lower surface in communication with the interior surface and the exterior surface. The plate comprises an opening operable to receive at least a portion of the exterior surface, said opening comprising a pair of flat surface portions operable to contact with the pair of flat surface portions of the bushing.

In another exemplary embodiment, an orthopedic plate assembly may comprise a fastener, a first bushing, a second bushing and a plate. The fastener may comprise a head and an elongated body connected at one end to the head. The first bushing may comprise an interior surface operable to receive the fastener head and a notch operable to contact against the fastener head. The second bushing comprises an interior surface operable to receive at least a portion of an exterior surface of the first bushing, an exterior surface comprising a pair of flat surface portions disposed about opposite sides of the second bushing, an upper surface in communication with the interior surface and the exterior surface of the second bushing, and a lower surface in communication with the interior surface and the exterior surface of the second bushing. The plate comprises an opening operable to receive at least a portion of the exterior surface of the second bushing, said opening comprising a pair of flat surface portions operable to contact with the pair of flat surface portions of the second bushing.

A fastener assembly according to another exemplary embodiment is operable to be received into an opening defined in an orthopedic plate. The fastener assembly comprises a fastener comprising a head and an elongated body connected at one end to the head. The fastener assembly also comprises a bushing. The bushing comprises an interior surface operable to receive at least a portion of the fastener head, an exterior surface operable to be received by the opening, and a notch forming a portion of the interior surface, said notch actuatable to contact against the fastener head.

An orthopedic plate assembly according to yet another exemplary embodiment is operable to receive a fastener element. The orthopedic plate assembly comprises a plate and a bushing. The plate comprises an opening, said opening comprising a pair of flat surface portions disposed about opposite sides of the opening. The bushing is operable to be received in the opening. The bushing comprises an interior surface operable to receive at least a portion of the fastener, an exterior surface comprising a pair of flat surface portions operable to contact with the flat surface portions of the opening, an upper surface in communication with the interior surface and the exterior surface, and a lower surface in communication with the interior surface and the exterior surface.

BRIEF DESCRIPTION OF THE DRAWINGS

For a more complete understanding of the present disclosure and its advantages, reference is now made to the following description taken in conjunction with the accompanying drawings, in which like reference numbers indicate like features, and.

Although similar reference numbers may be used to refer to similar elements for convenience, it can be appreciated that each of the various example embodiments may be considered to be distinct variations.

DETAILED DESCRIPTION

Exemplary embodiments will now be described hereinafter with reference to the accompanying figures, which form a part hereof, and which illustrate examples by which the exemplary embodiments, and equivalents thereof, may be practiced. As used in the disclosures and the appended claims, the terms "embodiment," "example embodiment" and "exemplary embodiment" do not necessarily refer to a single embodiment, although it may, and various example embodiments, and equivalents thereof, may be readily combined and interchanged, without departing from the scope or spirit of present embodiments. Furthermore, the terminology as used herein is for the purpose of describing example embodiments only and is not intended to be limitations of the embodiments. In this respect, as used herein, the term "plate" may refer to any substantially flat structure or any other three-dimensional structure, and equivalents thereof, including those structures having one or more portions that are not substantially flat along one or more axis. Furthermore, as used herein, the terms "opening," "recess," "aperture," and equivalents thereof, may include any hole, space, area, indentation, channel, slot, bore, and equivalents thereof, that is substantially round, oval, square, rectangular, hexagonal, and/or of any other shape, and/or combinations thereof, and may be defined by a partial, substantial or complete surrounding of a material surface. Furthermore, as used herein, the term "in" may include "in" and "on," and the terms "a," "an" and "the" may include singular and plural references. Furthermore, as used herein, the term "by" may also mean "from," depending on the context. Furthermore, as used herein, the term "if" may also mean "when" or "upon," depending on the context. Furthermore, as used herein, the words "and/or" may refer to and encompass any and all possible combinations of one or more of the associated listed items.

Figure 1:
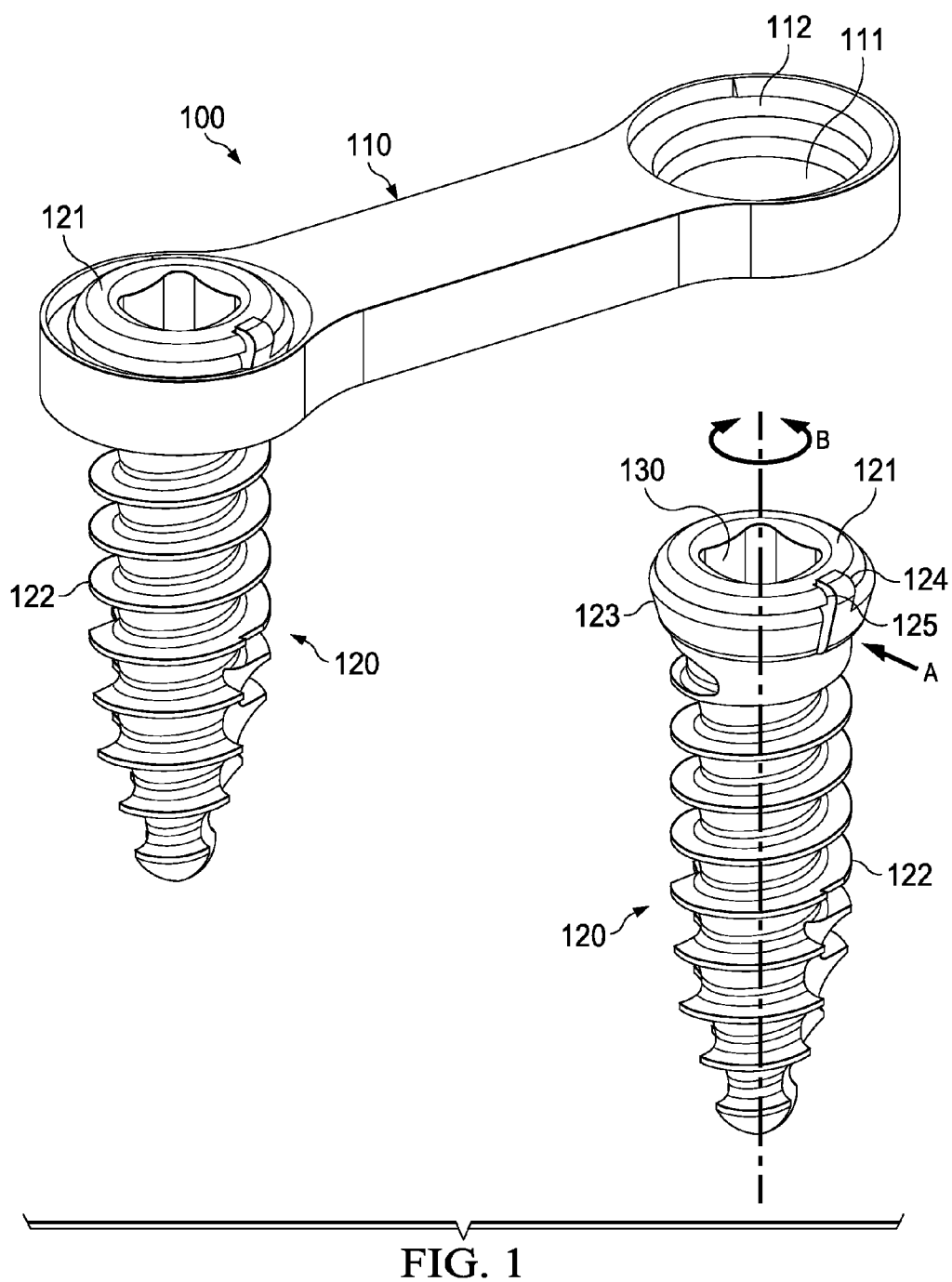
FIG. 1 is a perspective view of an example embodiment of an orthopedic plate assembly.
Figure 2:
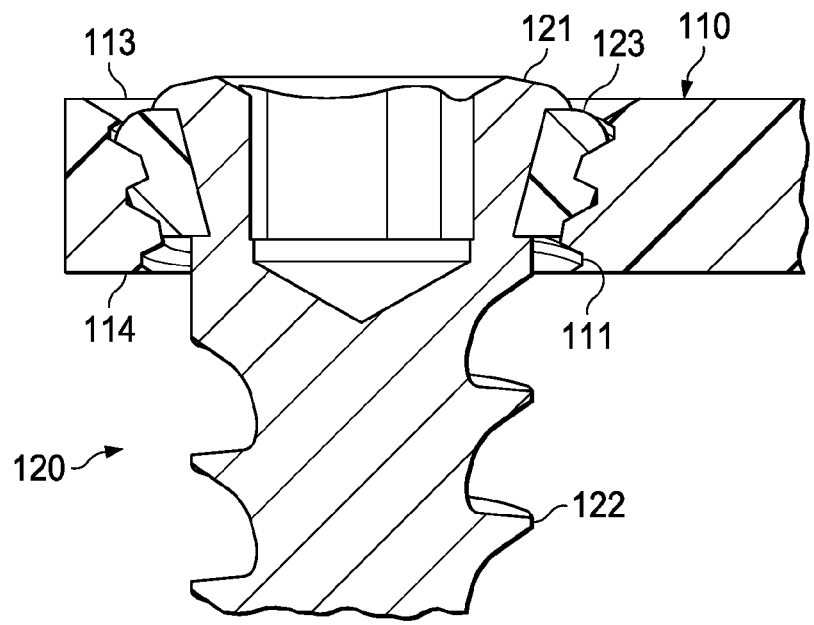
FIG. 2 is a cross-sectional view of an example embodiment of an orthopedic plate assembly.

Reference is now made to an exemplary embodiment of an orthopedic plate and fastener element assembly (100) illustrated in FIGS. 1-2. As shown in FIG. 1, the orthopedic plate comprises a body (110) and two openings (111) defined in the body (110). In exemplary embodiments, the body (110) may include more than two openings (111) depending on the specific patient and/or required treatment. Each opening (111) is operable to receive a corresponding fastener element (120), such as an anchor screw. As illustrated in FIG. 2, each opening (111) may be tapered in such a way that the opening about the upper surface (113), which is operable to receive a fastener element (120), is larger than the opening about the lower surface (114). The body (110) may be a substantially solid body, a substantially hollow body, an interconnection of substantially solid and/or hollow portions, or equivalents thereof, operable to enable connectivity between the openings (111). The body (110) may also include one or more portions that are of internally dynamizing constructs, or equivalents thereof, which enable the separation distances between openings (111) to adaptively change with time. For example, the two openings (111) depicted in FIG. 1 may come closer together over time as a bone fracture heals.

An exemplary embodiment of a fastener element (120) comprises a head (121) and a body (122). Preferably, the fastener element (120) comprises a threaded body (122), such as the threaded screw depicted in FIG. 1. Example embodiments of the body (122) of the fastener element (120) may be described as a threaded screw body, although the descriptions will also be equally applicable to example embodiments that are provided with fastener bodies of other shapes, forms and anchoring methods. The openings (111) of the orthopedic plate (110) for receiving threaded screw-type fastener elements (120) will also include corresponding threaded walls (112), or equivalents thereof. The fastener head (121) further comprises a top portion (130) adapted to connect to a fastening tool, such as an orthopedic screw driver, and a side portion. The bottom portion of the fastener head (121) attaches to the body (122). It is to be understood that the head (121) and the body (122) may be constructed using the same, similar or different materials, and may be formed as one element or two or more separate elements that are securely attached together to form the fastener element (120).

A bushing (123) can be attached to at least a portion of the fastener element head (121) in example embodiments. The bushing (123) is preferably constructed with a material that is softer than the material of the fastener head (121), and/or the same type of material as the fastener head (121) but softer. Furthermore, the material forming the bushing (123) is preferably a different and/or softer material than the material of the surface forming the opening (112) of the orthopedic plate (110), which is used for receiving the fastener element (120) in example embodiments. The bushing (123) may be formed from a polymer material such as polyether ether ketone (PEEK), ultra-high-molecular-weight polyethylene (UHMWP), high-modulus polyethylene (HMPE), and/or high-performance polyethylene (HPPE), or the like.

Although FIG. 1 depicts the bushing (123) as an integrated part of the fastener element (120), in some embodiments, the bushing (123) may also be one or more separate elements operable to be attached to the fastener element (120), preferably about at least a side portion of the fastener head (121), and/or operable to be inserted and/or threaded into the opening (111) of the orthopedic plate (110).

In exemplary embodiments, the bushing (123) further includes a notch portion (124). Hereinafter, the notch portion (124) will be described as an integrated part of the bushing (123) and constructed with substantially the same material as the bushing (123). It is to be understood, however, that descriptions herein will also be equally applicable to example embodiments of the notch portion (124) that are separate elements attachable to the bushing (123) and/or fastener head (121), and/or an integrated part of the fastener head (121). Furthermore, the notch portion (124) may be constructed with a different material than the bushing (123), such as a harder or softer material, and/or the same type of material as the bushing (123) but with different hardness, in some example embodiments.

When the bushing (123), the notch portion (124) and the fastener element (120) are collectively attached and/or integrated together (hereinafter collectively referred to as "fastener assembly,") example embodiments of the notch portion (124) may comprise an interior surface operable to form a substantially flat, recessed or protruding portion (shown in FIG. 1) of the interior surface of the bushing (123). Furthermore, example embodiments of the notch portion (124) may comprise an exterior surface operable to form a substantially flat, recessed or protruding portion (shown in FIG. 1) of the exterior surface of the bushing (123). It is to be understood herein that references to said interior surface will be directed to the surface operable to receive and contact at least a portion of the fastener head (121). Furthermore, references to said exterior surface will be directed to the surface operable to be received by and contact with at least a portion of the surface forming the opening (111) of the orthopedic plate (110).

The notch portion (124) is operable to be actuated in such a way so as to be pressed or contacted against a portion of the fastener head (121), which effectively provides for a firm hold of the fastener head (121) relative to the bushing (123). Actuating the notch portion (124) is achievable when a sufficient inwardly force is applied about the exterior portion of the notch portion (124), as depicted by the arrow A in FIG. 1, and/or about one or more portions of the exterior portion of the bushing (123), inwardly towards the fastener head (121). In this regard, when the fastener assembly is threaded into an opening (111) of the orthopedic plate (110), the interior walls, or equivalents thereof, of the opening (111) will effectively provide the said inwardly force to actuate the notch portion (124). Furthermore, the said inwardly force is preferably operable to compress the bushing (123) and/or notch portion (124), which are preferably constructed of a material that is softer as previously described, to firmly hold the fastener assembly relative to the orthopedic plate (110). Effectively, the fastener assembly is firmly held and precluded from rotating relative to the bushing (123), as depicted by the arrow B in FIG. 1. In exemplary embodiments, the fastener head (121) may include a corresponding recessed portion (125) operable to receive the interior surface of the notch portion (124).

Reference is now made to the bushing (123), the notch portion (124), the fastener head (121) and the opening (111) of the orthopedic plate (110) used for receiving the combination of the fastener head (121), the notch portion (124) and the bushing (123). Collectively, these elements are appropriately sized and shaped in such a way that the bushing (123) firmly attaches to and substantially surrounds the side of the fastener head (121). Furthermore, the combined size and shape of the bushing (123), the notch portion (124) and the fastener head (121) will be selected so as to not completely pass through the opening (114) of the plate (110). More specifically, when completely or substantially threaded into the opening (111) from opening (113), the fastener assembly will be substantially and firmly housed within the tapered opening (111). Because the bushing (123) and/or the notch portion (124) are constructed of a softer material than the materials of the fastener element (120) and the proximate portion of the plate (110) defining the opening (112), the structural shape of the bushing (123) is adaptively changeable or "compressible" when a user applies force in threading the combined bushing (123) and fastener (120) into the opening (111) of the orthopedic plate (110). Effectively, the combination of the adaptive bushing (123) and the actuatable notch portion (124) will prevent the fastener element (120) from backing out from the opening (111) of the orthopedic plate (110) when the combined bushing (123), notch portion (124) and fastener element (120) is completely or substantially threaded into the opening (111) and the actuated notch portion (124) is received by the recessed portion (125) of the fastener head (121).

Figure 3A:
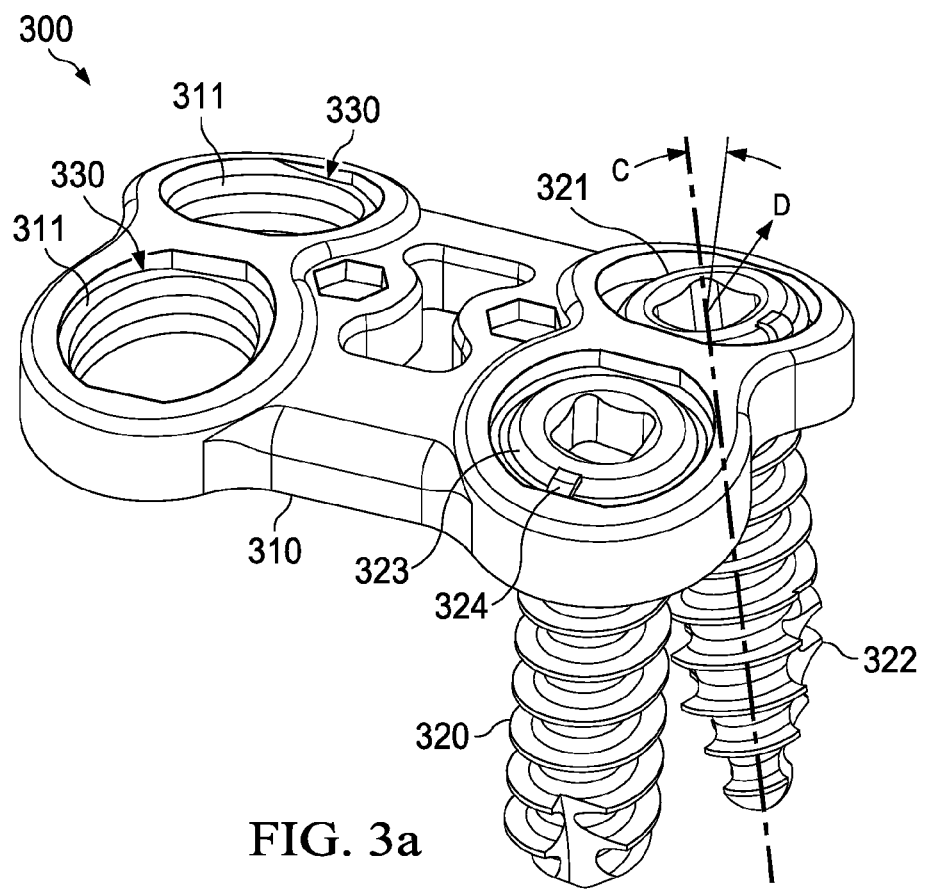
FIG. 3A is a perspective view of an example embodiment of an orthopedic plate assembly.
Figure 3B:
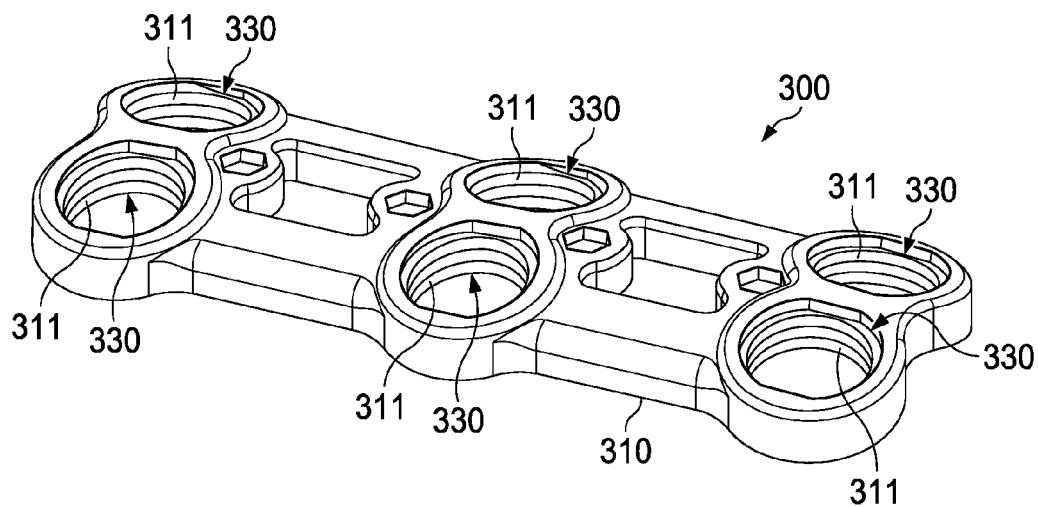
FIG. 3B is a perspective view of an example embodiment of an orthopedic plate assembly.
Figure 5:
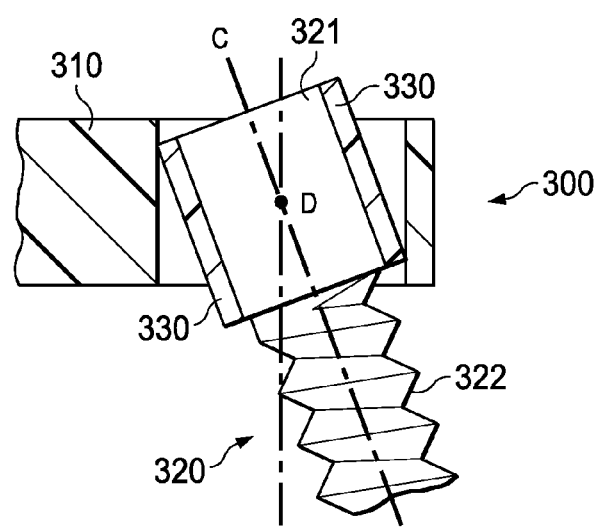
FIG. 5 is a cross-sectional view of an example embodiment of an orthopedic plate assembly.
Figure 4:
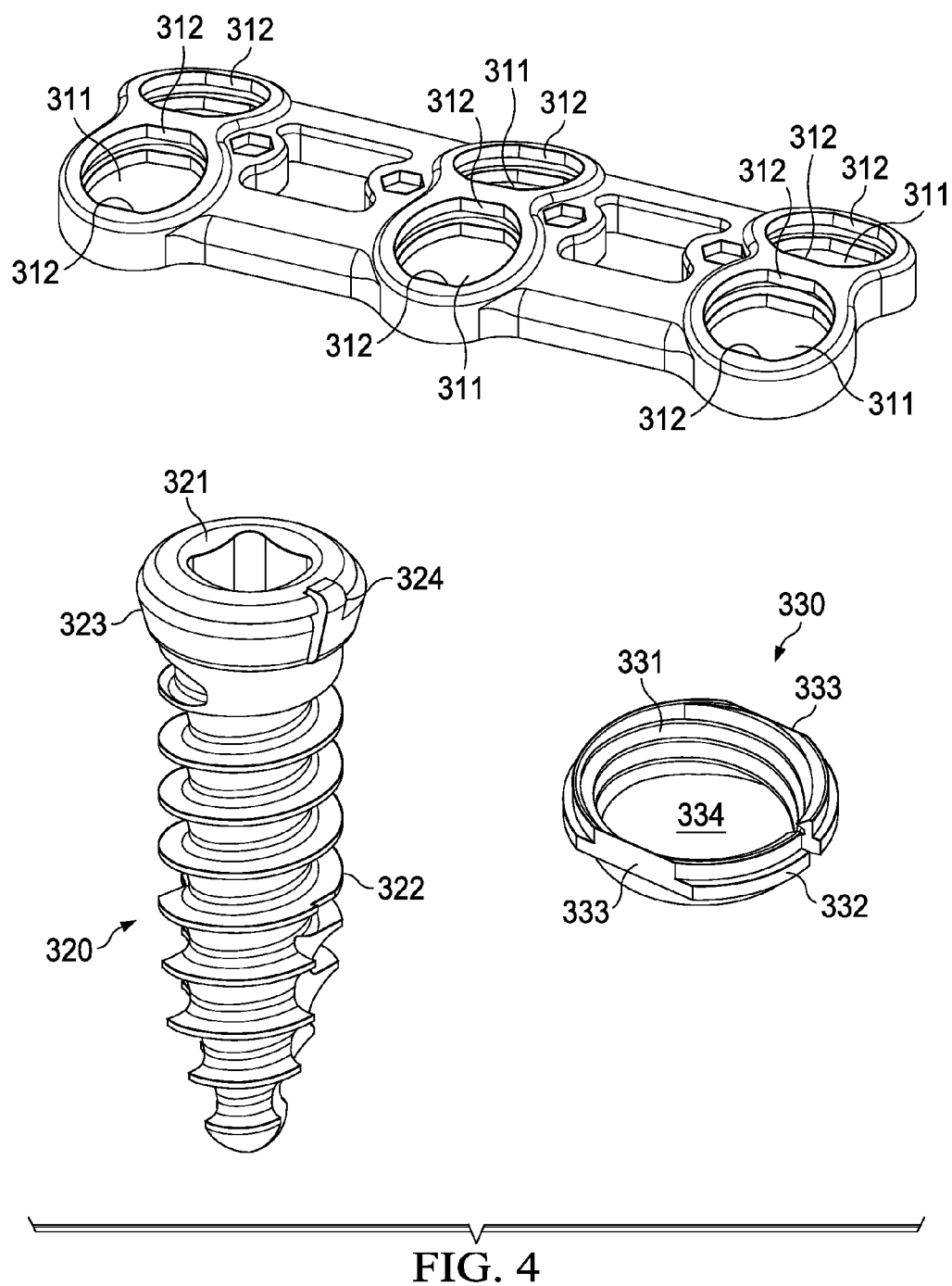
FIG. 4 is another perspective view of an example embodiment of an orthopedic plate assembly.

Reference is now made to exemplary embodiments of an orthopedic plate assembly (300) illustrated in FIGS. 3-5. As shown in FIG. 3a, the orthopedic plate comprises a body (310) and four openings (311) defined in the body (310). In some embodiments, the body (310) may include more or less than four openings (311), such as the orthopedic plate illustrated in FIG. 3b having six openings (311). Each opening (311) is operable to receive a corresponding fastener element (320), such as an anchor screw. Preferably, each opening (311) is tapered, such as previously described and illustrated in FIG. 2. It is to be understood herein that the body (310) may be a substantially solid body, a substantially hollow body, an interconnection of substantially solid and/or hollow portions, or equivalents thereof, operable to enable connectivity between the openings (311). The body (310) may also include one or more portions that are of internally dynamizing constructs, or equivalents thereof, which enable the separation distances between openings (311) to adaptively change with time. For example, two or more openings (311) depicted in FIGS. 3-4 may come closer together over time as a bone fracture heals.

The orthopedic plate assembly (300) may utilize any appropriately shaped and sized fastener element. In an exemplary embodiment, the fastener element (320) comprises a head (321) and a body (322). Preferably, the fastener element (320) comprises a threaded body (322), such as the threaded screw depicted in FIGS. 1 and 3. Hereinafter, example embodiments of the fastener element (320) will be described as a threaded screw, although the descriptions will also be equally applicable to example embodiments that are provided with fastener elements (320) of other shapes, forms and anchoring methods. The fastener head (321) further comprises a top portion for receiving a fastening tool, such as an orthopedic screw driver, and a side portion. The bottom portion of the fastener head (321) attaches to the body (322). The head (321) and the body (322) may be constructed using the same, similar or different materials, and may be formed as one element or two or more separate elements that are securely attached together to form the fastener element (120).

In exemplary embodiments, one or more of the openings (311) of the orthopedic plate (310) are operable to house a bushing (330). In some example embodiments, each opening (311) of the orthopedic plate (310) is operable to house a bushing (330). Once housed in the opening (311), the interior surface (331) of the bushing (330) effectively defines the opening (311) of the orthopedic plate (310). Each housed bushing (330) is then operable to securely receive a fastener element (320). In example embodiments wherein the fastener element (320) comprises a threaded body (322), such as the threaded screw depicted in FIG. 3, the interior surface (331) of the bushing (330) may also comprise a corresponding threaded surface. Unlike bushing (123) previously described and illustrated in FIGS. 1-2, bushing (330) will be preferably constructed of harder material than bushing (123) and will not be adaptively changeable and/or "compressible" like bushing (123), particularly when a user applies force to thread a fastener (320) into a housed bushing (330).

The exterior surface (332, 333) of each bushing (330) includes at least a pair of flat surface portions (333) disposed on opposite sides of the bushing (330), as illustrated in FIG. 4. An opening (311) of the orthopedic plate (310) operable to receive the bushing (330) is correspondingly provided with a pair of flat surface portions (312) disposed on opposite sides of the opening (311). Together, the flat surface portions (312, 333) are appropriately sized and shaped to substantially contact with one another and rotatably slide relative to one another about a centerpoint of the flat surface portion (333). The purpose of the corresponding pairs of flat surface portions (312, 333) is two fold. Firstly, the corresponding flat surface portions (312, 333) are operable to enable the bushing (330) to pivot (ie. the previously described rotatably sliding movement) within a certain cone of angulation C about an axis D formed by a line drawn between the two opposing flat surface portions (312 or 333), as depicted in FIG. 3A. The angle C and axis D are also depicted in the cross-sectional illustration of FIG. 5. In enabling such pivoting, a fastener element (320) is enabled to anchor into the bone at an angle that is not substantially perpendicular to the proximate plane of the bone, preferably within the said cone of angulation C. Secondly, the corresponding flat surface portions (312, 333) are operable to prevent the bushing (330) from rotating in a plane formed by the bushing (330). Specifically, the flat surface portions (312, 333) effectively prevent the bushing (330) from rotating along with a fastener element (320) when the fastener element (320) is rotatably threaded into the bushing (330). The flat surface portions (312, 333) are operable to prevent such rotation irrespective of whether or to what degree the bushing (330) is pivoted about the axis D.

Although FIG. 4 depicts the bushing (330) as a separate element, it is to be understood that the bushing (330) may also be integrated with or attached to the opening (311) of the orthopedic plate (310) or operable to be attached to the fastener element (320).

Example embodiments of the fastener element (120) and the bushing (123), which were previously described and illustrated in FIGS. 1-2, and equivalents thereof, may also be utilized with the orthopedic plate (310) and bushing (330), and equivalents thereof. Example embodiments will be operable to enable the fastener element (120) to select an entry angle C to anchor into the bone, prevent the bushing (330) from rotating along with a fastener element (120) when the fastener element (120) is rotatably threaded into the bushing (330), and also prevent a completely or substantially threaded fastener element (120) from backing out from an opening (311) of the orthopedic plate (310).

Figure 6:
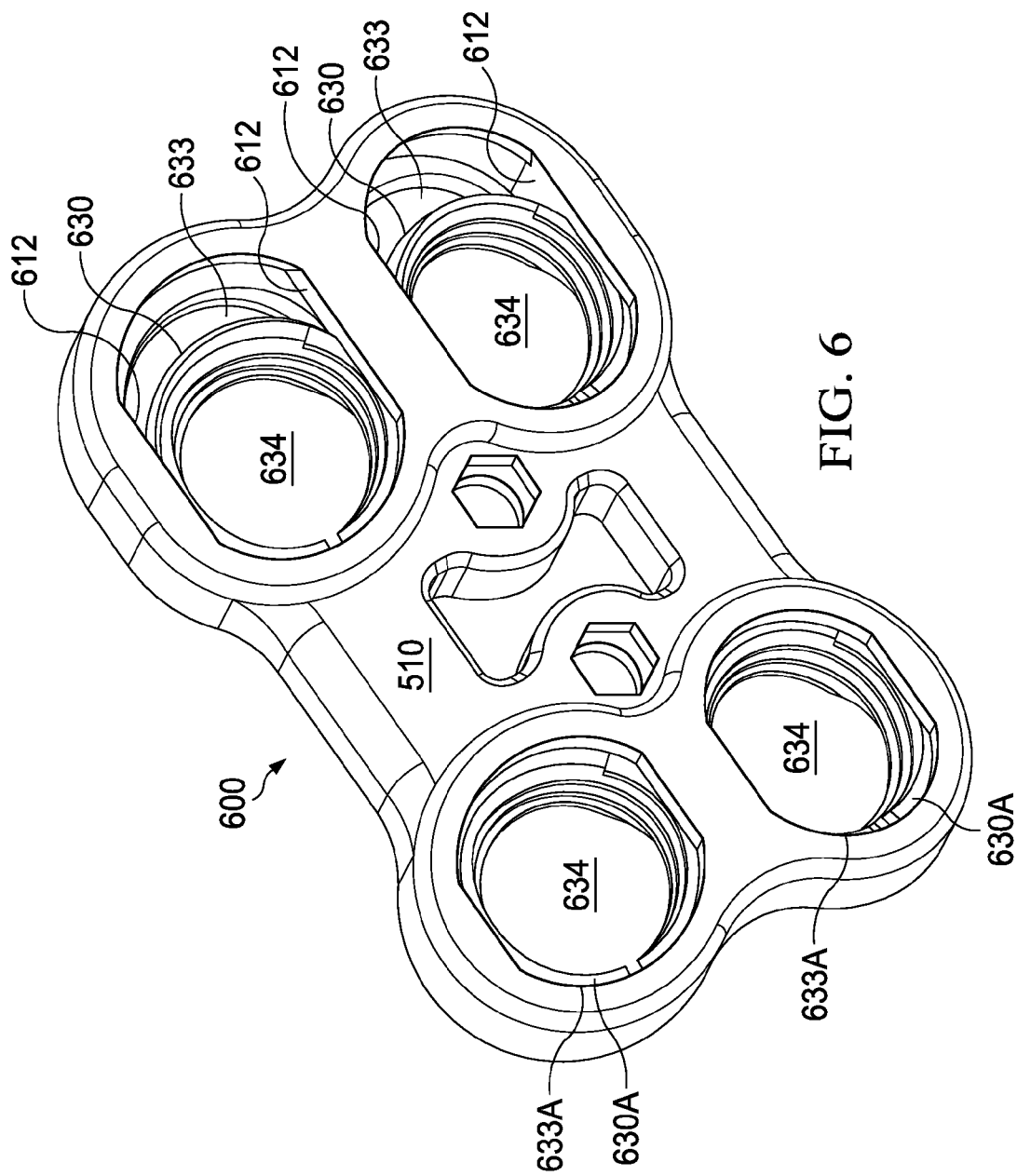
FIG. 6 is a perspective view of an example embodiment of an orthopedic plate assembly.

The orthopedic plate assembly (600) may include one or more openings (633) defined in the orthopedic plate (610) comprising a shape and/or size that is different from the shape and/or size of the bushing (630). In the example embodiment illustrated in FIG. 6, there are two exemplary openings (633), each shaped in the form of a slot having two elongated opposing flat surface portions (612) on each elongated side. The two flat surface portions (612) are operable to effectively contact with the two flat surface portions (not shown) of the bushing (630) in an equivalent manner as previously described and illustrated in FIGS. 3-5. That is, embodiments are operable to enable a fastener element (120, 320) to select an entry angle C to anchor into the bone and also prevent the bushing (630) from rotating along with a fastener element (120, 320) when the fastener element (120, 320) is rotatably threaded into the bushing (630). When applying embodiments of the fastener element (120, 320) previously described and illustrated in FIGS. 1-5, example embodiments will also be operable to prevent a completely or substantially threaded fastener element (120, 320) from backing out from the orthopedic plate (510). In incorporating the elongated slot-shaped opening (633), or equivalents thereof, example embodiments further enable the bone, or portions thereof, that is anchored by the fastener element (not shown) threaded into the bushings (630) to translate along the elongated slot.

While various embodiments in accordance with the disclosed principles have been described above, it should be understood that they have been presented by way of example only, and are not limiting. Thus, the breadth and scope of the invention(s) should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically, a description of a technology in the "Background" is not to be construed as an admission that technology is prior art to any invention(s) in this disclosure. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings herein.

What is claimed is:

1. An orthopedic plate assembly comprising:
   a fastener comprising a head and an elongated body connected at one end to the head;
   a bushing comprising:
      an interior surface operable to receive at least a portion of the fastener head; and
      a notch actuatable to contact against the fastener head upon inward force being applied about an exterior portion of the notch towards the fastener head, the inward force compressing the notch; and
   a plate comprising an opening operable to receive at least a portion of an exterior surface of the bushing.

2. The orthopedic plate assembly of claim 1, wherein the notch is operable to prevent a backout of the fastener relative to the plate when a wall defining the opening actuates the notch to form a protruding portion of the interior surface.

3. The orthopedic plate assembly of claim 2, wherein the fastener head comprises at least one recess operable to receive the protruding portion when the notch is actuated.

4. The orthopedic plate assembly of claim 1, wherein the bushing is constructed of material that is softer than the materials of the fastener and the plate.

5. The orthopedic plate assembly of claim 4, wherein the softer material is selected from the group consisting of polyether ether ketone (PEEK), ultra-high-molecular-weight polyethylene (UHMWP), high-modulus polyethylene (HMPE), and high-performance polyethylene (HPPE).

6. An orthopedic plate assembly comprising:
a fastener;
a bushing comprising:
an interior surface operable to receive at least a portion of the fastener;
an exterior surface comprising a pair of flat surface portions disposed about opposite sides of the bushing, wherein the flat surface portions are chordal portions that intersect the exterior surface, wherein, when the bushing is received in the opening, the bushing is pivotable relative to the plate about an axis formed by the oppositely disposed flat surface portions;
an upper surface in communication with the interior surface and the exterior surface; and
a lower surface in communication with the interior surface and the exterior surface; and
a plate comprising an opening operable to receive at least a portion of the exterior surface, said opening comprising a pair of flat surface portions operable to contact with the pair of flat surface portions of the bushing.

7. The orthopedic plate assembly of claim 6, wherein, when the bushing is received in the opening, the bushing and the opening are in contact with each other at least about their respective flat surface portions.

8. The orthopedic plate assembly of claim 6, wherein, when the bushing is received in the opening, the flat surface portions of the bushing and the opening are operable to prevent the bushing from rotating relative to the plate.

9. An orthopedic plate assembly comprising:
a fastener comprising a head and an elongated body connected at one end to the head;
a first bushing comprising:
an interior surface operable to receive the fastener head; and
a notch actuatable to contact against the fastener head; and
a second bushing comprising:
an interior surface operable to receive at least a portion of an exterior surface of the first bushing;
an exterior surface comprising a pair of flat surface portions disposed about opposite sides of the second bushing;
an upper surface in communication with the interior surface and the exterior surface of the second bushing; and
a lower surface in communication with the interior surface and the exterior surface of the second bushing; and
a plate comprising an opening operable to receive at least a portion of the exterior surface of the second bushing, said opening comprising a pair of flat surface portions operable to contact with the pair of flat surface portions of the second bushing.

10. The orthopedic plate assembly of claim 9, wherein the notch is operable to prevent backout of the fastener relative to the second bushing when the interior surface of the second bushing actuates the notch to form a protruding portion of the interior surface of the first bushing.

11. The orthopedic plate assembly of claim 10, wherein the fastener head comprises at least one recess operable to receive the protruding portion when the notch is actuated.

12. The orthopedic plate assembly of claim 9, wherein the first bushing is constructed of material that is softer than the materials of the fastener and the second bushing.

13. The orthopedic plate assembly of claim 12, wherein the softer material is selected from the group consisting of polyether ether ketone (PEEK), ultra-high-molecular-weight polyethylene (UHMWP), high-modulus polyethylene (HMPE), and high-performance polyethylene (HPPE).

14. The orthopedic plate assembly of claim 9, wherein, when the second bushing is received in the opening, the second bushing and the opening are in contact with each other at least about their respective flat surface portions.

15. The orthopedic plate assembly of claim 9, wherein, when the second bushing is received in the opening, the second bushing is pivotable relative to the plate about an axis formed by the oppositely disposed flat surface portions.

16. The orthopedic plate assembly of claim 9, wherein, when the second bushing is received in the opening, the flat surface portions of the second bushing and the opening are operable to prevent the second bushing from rotating relative to the plate.

17. A fastener assembly operable to be received into an opening defined in an orthopedic plate, said fastener assembly comprising:
a fastener comprising a head and an elongated body connected at one end to the head; and
a bushing comprising an interior surface operable to receive at least a portion of the fastener head, an exterior surface operable to be received by the opening, and a notch forming a portion of the interior surface, said notch actuatable to contact against the fastener head upon inward force being applied about an exterior portion of the notch towards the fastener head, the inward force compressing the notch.

18. The fastener assembly of claim 17, wherein the notch is operable to prevent a backout rotation of the fastener relative to the orthopedic plate when a wall defining the opening actuates the notch to form a protruding portion of the interior surface.

19. The fastener assembly of claim 18, wherein the fastener head comprises at least one recess operable to receive the protruding portion when the notch is actuated.

20. The fastener assembly of claim 17, wherein the bushing is constructed of material that is softer than the materials of the fastener and the plate.

21. The fastener assembly of claim 20, wherein the softer material includes PEEK.

22. An orthopedic plate assembly operable to receive a fastener, said orthopedic plate assembly comprising:
a plate comprising an opening, said opening comprising a pair of flat surface portions disposed about opposite sides of the opening; and
a bushing operable to be received in the opening, said bushing comprising:
an interior surface operable to receive at least a portion of the fastener;

an exterior surface comprising a pair of flat surface portions operable to contact with the flat surface portions of the opening, wherein the flat surface portions are chordal portions that intersect the exterior surface, wherein, when the bushing is received in the opening, the bushing is pivotable relative to the plate about an axis formed by the oppositely disposed flat surface portions;

an upper surface in communication with the interior surface and the exterior surface; and a lower surface in communication with the interior surface and the exterior surface.

23. The orthopedic plate assembly of claim 22, wherein, when the bushing is received in the opening, the bushing and the opening are in contact with each other at least about their respective flat surface portions.

24. The orthopedic plate assembly of claim 22, wherein, when the bushing is received in the opening, the flat surface portions of the bushing and the opening are operable to prevent the bushing from rotating relative to the plate.

\* \* \* \* \*